US00PP31266P2

(12) United States Plant Patent
Pineau

(10) Patent No.: US PP31,266 P2
(45) Date of Patent: Dec. 24, 2019

(54) ***HIBISCUS* PLANT NAMED 'MINSYMACWHI 1'**

(50) Latin Name: *Hibiscus syriacus*
Varietal Denomination: MINSYPMACWHI1

(71) Applicant: Patrick Pineau, Saint Mathurin sur Loire (FR)

(72) Inventor: Patrick Pineau, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 16/350,723

(22) Filed: Dec. 20, 2018

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ..... A01H 5/02; A01H 6/60
See application file for complete search history.

*Primary Examiner* — Annette H Para
(74) *Attorney, Agent, or Firm* — Cassandra Bright

(57) ABSTRACT

A new and distinct *Hibiscus* cultivar named 'MINSYMACWHI1' is disclosed, characterized by large, white flowers with large red eyes. Plants are floriferous and tolerate wet conditions well. The new variety is a *Hibiscus*, normally produced as an outdoor garden or container plant.

3 Drawing Sheets

Figure 1:
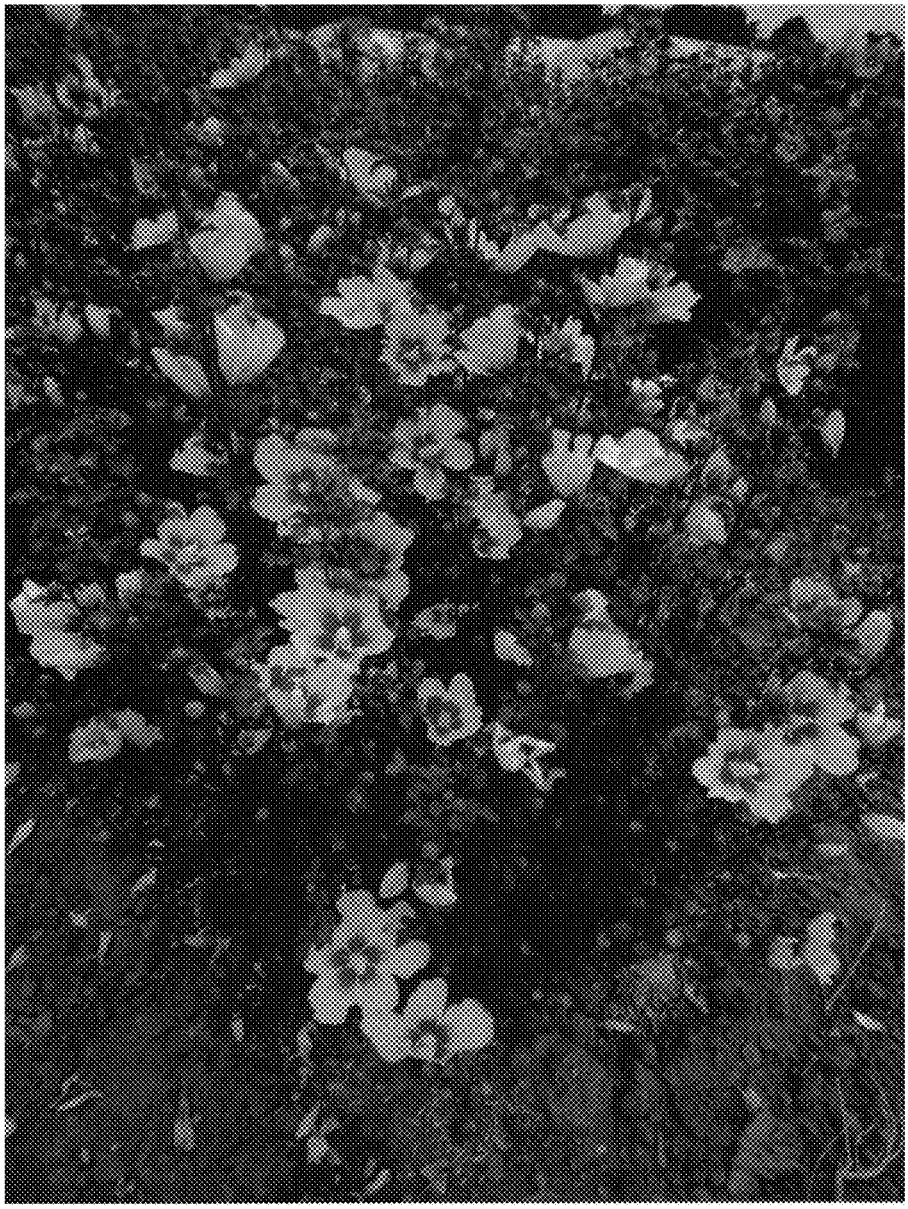

Latin name of the genus and species: *Hibiscus syriacus*. Variety denomination: 'MINSYMACWHI1'.

BACKGROUND OF THE INVENTION

The new *Hibiscus* cultivar is a product of a planned breeding program conducted by the inventor, Patrick Pineau. The objective of the breeding program was to new cultivars of *Hibiscus syriacus* with large flowers and healthy foliage. The cross resulting in this new variety was made during 2004.

The seed parent is the unpatented proprietary *Hibiscus syriacus* 'R2-30'. The pollen parent is the unpatented *Hibiscus syriacus* 'Minrosa'. The new variety was identified and selected as a potentially interesting selection in September 2008. Selection was made at a nursery in La Menitre, France.

Asexual reproduction of the new cultivar 'MINSYMACWHI1' was first performed in January 2009 in La Menitre, France, by grafting. Subsequent propagation has shown that the unique features of this cultivar are stable and reproduced true to type in 10 successive generations.

SUMMARY OF THE INVENTION

The cultivar 'MINSYMACWHI1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSYMACWHI1' These characteristics in combination distinguish 'MINSYMACWHI1' as a new and distinct *Hibiscus* cultivar:

1. Large white single flower with big red eye.
2. Erect plant form.
3. Well branched.
4. Vigorous.

PARENT COMPARISON

Plants of the new cultivar 'MINSYMACWHI1' are similar to plants of the seed parent variety in most horticultural characteristics, however, plants of the new cultivar 'MINSYMACWHI1' differ in the following;

1. Plants of the new variety have a dark eye, the seed parent does not have this eye.
2. Plants of the new variety have more branches than the seed parent.

Plants of the new cultivar 'MINSYMACWHI1' are similar to plants of the pollen parent variety in most horticultural characteristics, however, plants of the new cultivar 'MINSYMACWHI1' differ in the following;

1. 'Minsymacwhi1' is more vigorous and more branched than the pollen parent.
2. 'Minsymacwhi1' has less overlapping petals than the pollen parent.
3. 'Minsymacwhi1' has larger flowers than the pollen parent.
4. 'Minsymacwhi1' has white flowers with a red eye, the pollen parent has pink flowers.
5. 'Minsymacwhi1' has a higher ratio of basal blotch than pollen parent.

COMMERCIAL COMPARISON

Plants of the new cultivar 'MINSYMACWHI1' can be compared to the variety *Hibiscus* 'Minfren', unpatented. These varieties are similar in most horticultural characteristics however, 'MINSYMACWHI1' differs in the following:

1. 'Minsymacwhi1' has single flowers, while 'Minfren' has semi double flowers.
2. 'Minsymacwhi1' has fewer overlapping petals than 'Minfren'.
3. 'Minsymacwhi1' has larger flowers than 'Minfren'.

4. 'Minsymacwhi1' has a pink outside edge blush, not found on 'Minfen'.
5. 'Minsymacwhi1' has flat petals, 'Minfren' has ruffled petals.

Plants of the new cultivar 'MINSYMACWHI1' can also be compared to the variety *Hibiscus* 'Red Heart', unpatented. These varieties are similar in most horticultural characteristics however, 'MINSYMACWHI1' differs in the following:

1. 'Minsymacwhi1' is more vigorous and more branched than 'Red Heart'.
2. 'Minsymacwhi1' has deeper leaf lobing than 'Red heart'.
3. 'Minsymacwhi1' has fewer overlapping petals than 'Red Heart'.
4. 'Minsymacwhi1' has larger flowers than 'Red Heart'.
5. 'Minsymacwhi1' has a higher ratio of basal blotch than 'Red Heart'.
6. 'Minsymacwhi1' has pink outside edge blush, not found on 'Red Heart'.

BRIEF DESCRIPTION OF THE PHOTOGRAPHS

The accompanying photograph in FIG. 1 illustrates in full color a typical plant of 'MINSYMACWHI1' grown outdoors in La Menitre, France.

Figure 2:
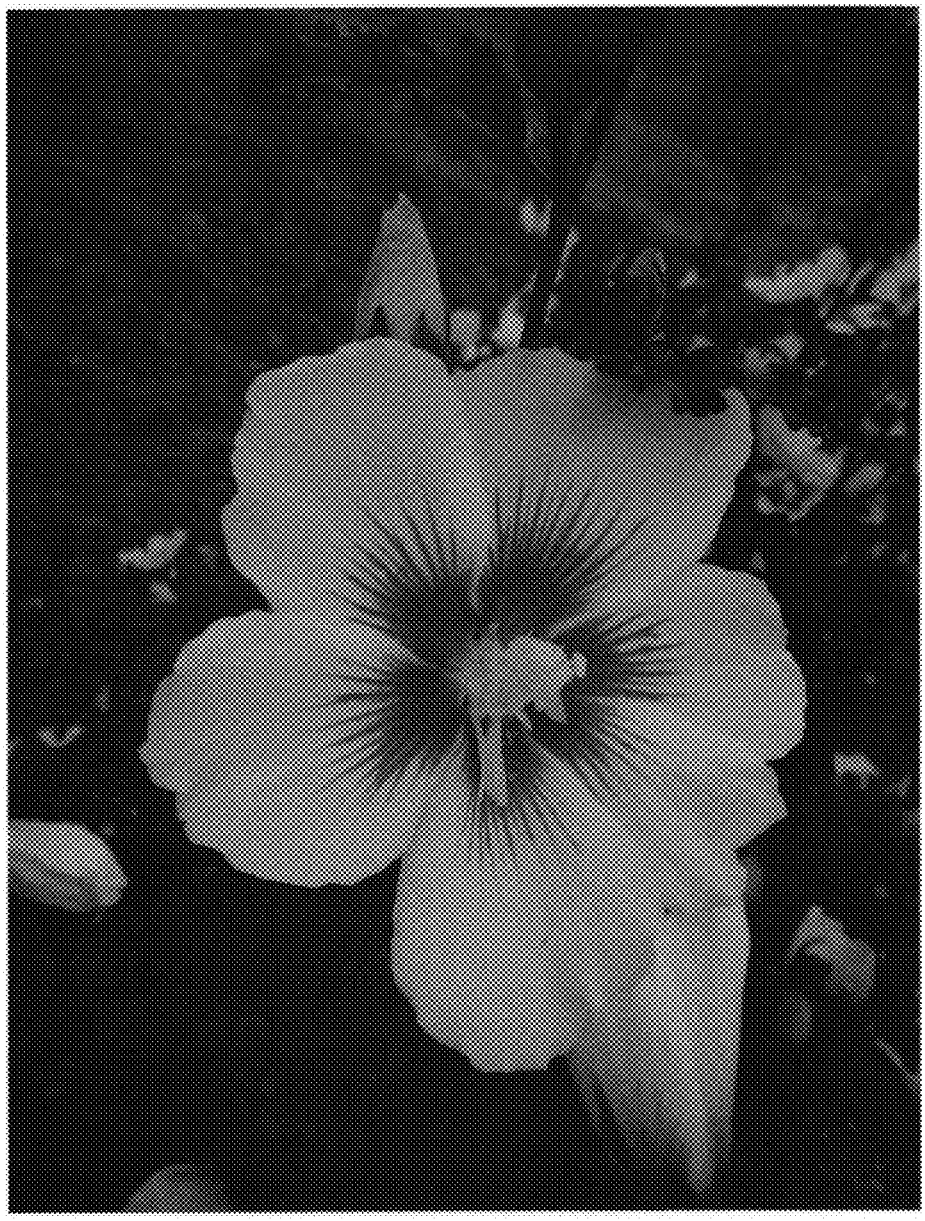

FIG. 2 illustrates in full color a typical flower of 'MINSYMACWHI1'.

Figure 3:
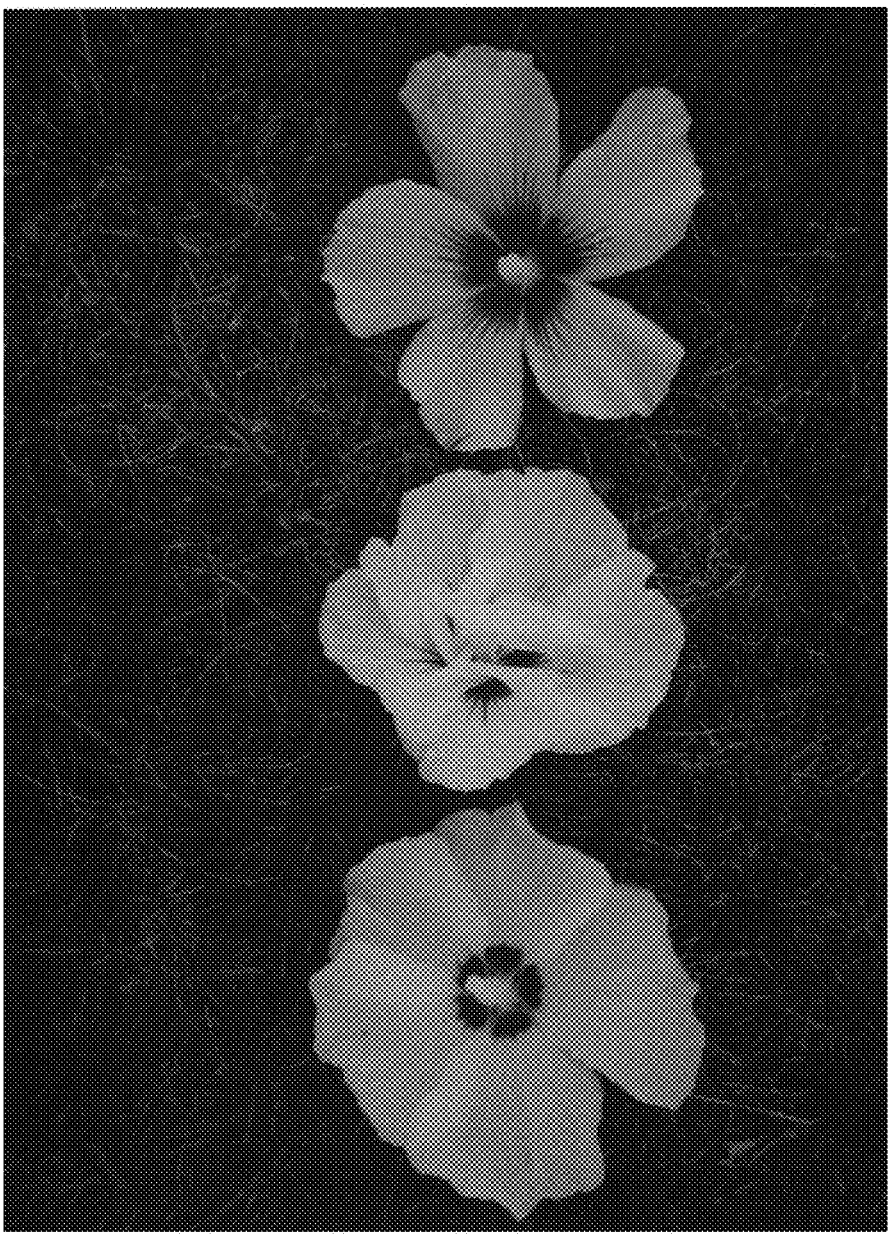

FIG. 3 is a comparison of three similar varieties. The top flower is 'MINSYMACHWHI1', the center flower is 'Minfren', the bottom flower is 'Red Heart'. Age of the plant photographed is approximately 10 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'MINSYMACWHI1' plants grown in an unheated polyhouse in La Menitre, France, under natural lighting. Measurements were taken during August of 2018. The plants were 10 years old in 20 cm containers. The growing temperature ranged from approximately −5° C. to 27° C. Measurements and numerical values represent averages of typical plant types.

Botanical classification: *Hibiscus syriacus* 'MINSYMACWHI1'.

PROPAGATION

Time to Initiate Roots: 20 days at approximately 25° C.

Root Description: Fibrous, medium root thickness. Tan/brown in color, not effectively measured with a color chart.

Time to produce a rooted young plant: About 90 days at 25° C.

PLANT

Plant type: Upright deciduous perennial shrub.

Age of Plant Described: Approximately 10 years old.

Growth Habit: Erect, vigorous.

Height: 100 cm.

Branching Characteristics: Well branched.

Length of Primary Lateral Branches: 90 cm.

Quantity of Lateral Branches: 8.

Characteristics of Primary Lateral Branches:

*Diameter.*—0.4 cm.

*Color.*—RHS Yellow-Green 147C.

Internode length: 5 cm.

FOLIAGE

Leaf:

*Arrangement.*—Alternate.

*Quantity.*—Approximately 25 per branch.

*Average Length.*—6 cm.

*Average Width.*—4 cm.

*Shape of blade.*—Ovate, deeply lobed. Most commonly 5 lobes.

*Apex.*—Acute.

*Base.*—Obtuse.

*Margin.*—Deeply serrate.

*Texture of top surface.*—Glabrous.

*Texture of bottom surface.*—Rough.

*Color.*—Young foliage upper side: RHS Green 137D. Young foliage under side: RHS Green 138A. Mature foliage upper side: RHS Green 137A. Mature foliage under side: RHS Green 137B.

*Fall or Winter coloration variance.*—Mature foliage upper side: None. Mature foliage under side: None.

*Venation.*—Type: Pinnate. Venation color upper side: RHS Green 143A. Venation color under side: RHS Green 143A.

*Petiole.*—Length: 1.5 cm. Diameter: 0.1 cm. Color: RHS Yellow-Green 143A.

FLOWER

Natural flowering season: July to September.

Flower type and habit: Solitary, rotate.

*Single, double, multiplex.*—Single.

*Petals overlapping.*—Moderately overlapping.

Rate of flower opening: 1 to 2 days from bud to fully opened flower.

Flower Longevity on Plant: 1 to 2 days.

Persistent or Self-Cleaning: Self-cleaning.

Bud:

*Shape.*—Ovate.

*Length.*—2 cm.

*Diameter.*—1.3 cm.

*Color.*—RHS Orange-White 159C flushed Red-Purple 63A.

Flower size:

*Diameter.*—12 cm.

*Depth.*—3 cm.

Petals:

*Quantity.*—5.

*Arrangement.*—Rotate.

*Length.*—6 cm.

*Width.*—4 cm.

*Shape.*—Ovate.

*Apex.*—Rounded. Irregular shallow lobes.

*Base.*—Tapered.

*Margin.*—Entire.

*Texture, upper and lower surfaces.*—

*Color.*—When opening, upper surface: RHS White 155D, flushed Red-Purple 64C. When opening, lower surface: RHS White 155D, flushed Red-Purple 64D. Fully opened, upper surface: RHS White 155A with pink edge blush Red-Purple 64D. Fully opened, lower surface: RHS White 155A, flushed 64D. Color basal blotch: RHS Red-Purple 59B. Ratio of basal blotch/petal size: ⅓. Feathering color: RHS Red-Purple 59B. Feathering size: 1.2 cm.

Sepals:

*Quantity.*—5 to 6.
*Length.*—1.5 cm.
*Width.*—0.7 cm.
*Shape.*—Ovate.
*Margin.*—Entire.
*Color.*—RHS Green 146C.

Peduncles:

*Length.*—3 cm.
*Diameter.*—0.3 cm.
*Angle.*—About 45° to the lateral branch.
*Strength.*—Strong.
*Texture.*—Glabrous.
*Color.*—RHS Green 146C.

Fragrance: None.

REPRODUCTIVE ORGANS

Stamens:

*Number.*—50.

Anthers:

*Shape.*—Irregular sphere.
*Length.*—0.3 cm.
*Color.*—Near RHS Yellow-White 158C.
*Pollen color.*—RHS Yellow 4D.
*Pollen amount.*—Abundant.

Pistil:

*Number.*—1.
*Length.*—3.5 cm.
*Style.*—Length: 3 cm. Color: Near RHS White 155C.
*Stigma.*—Shape: Rounded disc. Color: Near RHS White 155C.
*Ovary color.*—Near RHS Yellow-Green 145C.

OTHER CHARACTERISTICS

Seeds and fruits: Capsule, typically about 1 cm in diameter and length. Pubescent, colored near Grey-Brown 199B. Moderately abundant lightly pubescent seed.

Disease/pest resistance: Neither resistance nor susceptibility to normal diseases and pests of *Hibiscus syriacus* have been observed.

Temperature tolerance: Low temperature tolerance to at least USDA zone 4, high temperature tolerance to at least 40° C.

What is claimed is:

1. A new and distinct cultivar of *Hibiscus* plant named 'MINSYMACWHI1' as herein illustrated and described.

* * * * *